United States Patent [19]
Meissner et al.

[11] Patent Number: 5,981,215
[45] Date of Patent: Nov. 9, 1999

[54] HUMAN CRIPTIN GROWTH FACTOR

[75] Inventors: Paul S. Meissner, Barnesville; Timothy A. Coleman, Gaithersburg, both of Md.

[73] Assignee: Human Genome Sciences, Inc., Rockville, Md.

[21] Appl. No.: 08/471,371

[22] Filed: Jun. 6, 1995

[51] Int. Cl.⁶ .................. C07K 14/475; C12N 15/18; C12N 15/11; C12N 5/10
[52] U.S. Cl. ............. 435/69.1; 435/320.1; 435/325; 435/252.3; 435/254.11; 530/350; 530/300; 530/399; 536/23.5; 536/23.51; 536/23.1
[58] Field of Search .................. 435/69.4, 320.1, 435/240.2, 252.3, 254.11, 69.1, 325, 348; 530/399, 300, 350; 536/23.51, 24.3

[56] References Cited

U.S. PATENT DOCUMENTS

| | | | |
|---|---|---|---|
| 5,256,643 | 10/1993 | Persico et al. | 514/12 |
| 5,264,557 | 11/1993 | Salomon et al. | 530/399 |
| 5,688,936 | 11/1997 | Edwards et al. | 536/23.5 |
| 5,766,923 | 5/1995 | Kirschner et al. | 453/252.3 |

OTHER PUBLICATIONS

Lerner, R.A., Antibodies of predetermined specificity in biology and medicine, Adv. Immunol., 36: 1–44 1984.
Ciccodicola et al. (1989) Molecular characterization of a gene of the 'EGF family' expressed in undifferentiated human teratocarahoma cells. EMBO J. 8(7):1987–1991.

*Primary Examiner*—Lorraine Spector
*Assistant Examiner*—Claire M. Kaufman
*Attorney, Agent, or Firm*—Kenley K. Hoover

[57] ABSTRACT

A human Criptin Growth Factor polypeptide (CGF) and DNA (RNA) encoding such polypeptide and a procedure for producing such polypeptide by recombinant techniques is disclosed. Also disclosed are methods for utilizing such polypeptide for wound healing or tissue regeneration, stimulating implant fixation and angiogenesis. Antagonist against such polypeptides and their use as a therapeutic to treat and/or prevent neoplasia such as tumors is also disclosed. Diagnostic assays for identifying mutations in CGF nucleic acid sequences and altered levels of the CGF for the detection of cancer are also disclosed.

48 Claims, 2 Drawing Sheets

```
  1 ATGCAGAAGACTCTTCAAGATTCAGCTTTCCTGGAAACTGATCTTCAATGCACTAAGAGA   60

61 AGGAGACTCTCAAACCCAAAAATGACCTGGAGGCACCATGTCAGGCTTCTGTTTACGGTC  120
  1                           M  T  W  R  H  H  V  R  L  L  F  T  V    13

121 AGTTTGGCATTACAGATCATCAATTTGGGAAACAGCTATCAAAGAGAGAAACATAACGGC  180
 14  S  L  A  L  Q  I  I  N  L  G  N  S  Y  Q  R  E  K  H  N  G     33

181 GGTAGAGAGGAAGTCACCAAGGTTGCCACTCAGAAGCACCGACAGTCACCGCTCAACTGG  240
 34  G  R  E  E  V  T  K  V  A  T  Q  K  H  R  Q  S  P  L  N  W     53

241 ACCTCCAGTCATTTCGGAGAGGTGACTGGGAGCGCCGAGGGCTGGGGGCCGGAGGAGCCG  300
 54  T  S  S  H  F  G  E  V  T  G  S  A  E  G  W  G  P  E  E  P     73

301 CTCCCCTACTCCCGGGCTTTCGGAGAGGGTGCGTCCGCGCGGCCGCGCTGCTGCAGGAAC  360
 74  L  P  Y  S  R  A  F  G  E  G  A  S  A  R  P  C  C  R  N     93

361 GGCGGTACCTGCGTGCTGGGCAGCTTCTGCGTGTGCCCGGCCCACTTCACCGGCCGCTAC  420
 94  G  G  T  C  V  L  G  S  F  C  V  C  P  A  H  F  T  G  R  Y    113

421 TGCGAGCATGACCAGAGGCGCAGTGAATGCGGCGCCCTGGAGCACGGAGCCTGGACCCTC  480
114  C  E  H  D  Q  R  R  S  E  C  G  A  L  E  H  G  A  W  T  L    133

481 CGCGCCTGCCACCTCTGCAGGTGCATCTTCGGGGCCCTGCACTGCCTCCCCCTCCAGACG  540
134  R  A  C  H  L  C  R  C  I  F  G  A  L  H  C  L  P  L  Q  T    153

541 CCTGACCGCTGTGACCCGAAAGACTTCCTGGCCTCCCACGCTCACGGGCCGAGCGCCGGG  600
154  P  D  R  C  D  P  K  D  F  L  A  S  H  A  H  G  P  S  A  G    173

601 GGCGCGCCCAGCCTGCTACTCTTGCTGCCCTGCGCAACTCCTGCACCGGCCTCCTGCGCC  660
174  G  A  P  S  L  L  L  L  L  P  C  A  T  P  A  P  A  S  C  A    193

661 CGGATGCGCCCGCGCACCCTCGGTCCCTGGTCCCTTCCGTCCTCCAGCGGGAGCGGCGCC  720
194  R  M  R  P  R  T  L  G  P  W  S  L  P  S  S  S  G  S  G  A    213

721 CCTGCGGAAGGCCGGGACTTGGGCATCGCCTTTAATTTTCTATGTTGTAAATAA        774
214  P  A  E  G  R  D  L  G  I  A  F  N  F  L  C  C  K  *         231
```

FIG. 1

```
            1                                                    50
criptin     MTWRHHVRLL FTVSLALQI. ..INLGNSYQ REKHNGGREE VTKVATQKHR
cripto      MDCRKMARFS YSVIWIMAIS KVFELGLVAG LGHQEFARPS RGYLAFRDDS 51                                                  100
criptin     QSPLNWTSSH FGEVTGSAEG WGPEEPLPYS RAFGEGASAR PRCCRNGGTC
cripto      IWPQE..... EPAIRPRSSQ RVPPMGIQHS KELNRT.... ..CCLNGGTC 101                                                 150
criptin     VLGSFCVCPA HFTGRYCEHD QRRSECGALE HGAWTLRACH LCRCIFGALH
cripto      MLGSFCACPP SFYGRNCEHD VRKENCGSVP HDTWLPKKCS LCKCWHGQLR 151                                                 200
criptin     CLPLQTPDRC DP....KDFL ASHAHGPSAG GAPSLLLLLP CATPAPASCA
cripto      CFPQAFLPGC DGLVMDEHLV ASRTPELPPS ARTTTFMLVG ICLSIQSYY.

201                         237
criptin     RMRPRTLGPW SLPSSSGSGA PAEGRDLGIA FNFLCCK
cripto      .......... .......... .......... .......
```

Note: Conserved Cysteine residues are shown in BOLD.

FIG. 2

HUMAN CRIPTIN GROWTH FACTOR

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as a human Criptin Growth Factor, sometimes hereinafter referred to as "CGF". The invention also relates to inhibiting the action of such polypeptides.

Growth factors and other mitogens, including transforming oncogenes, are capable of rapidly inducing a complex set of genes to be expressed by certain cells (Lau, L. F. and Nathans, D., *Molecular Aspects of Cellular Regulation*, 6: 165–202 (1991). These genes, which have been named immediate early or early response genes, are transcriptionally activated within minutes after contact with a growth factor or mitogen, independent of de novo protein synthesis. A group of these immediate early genes encodes secreted, extracellular proteins which are needed for coordination of complex biological processes such as differentiation and proliferation, regeneration and wound healing (Ryseck, R. P. et al, *Cell Growth Differ.*, 2: 235–233 (1991).

The expression of these immediate early genes act as "third messengers" in the cascade of events triggered by growth factors. It is also thought that they are needed to integrate and coordinate complex biological processes, such as differentiation and wound healing in which cell proliferation is a common event.

The criptin growth factor is overexpressed and secreted by certain types of cancer cells, for example, by pancreatic cancers.

The CGF of the present invention shows amino acid sequence homology to the cripto growth factor disclosed in U.S. Pat. No. 5,256,643 which is hereby incorporated by reference in its entirety. The cripto growth factor is one of the useful tumor markers known. Cripto is often upregulated in colon cancers and is expressed in pancreatic cancers.

In accordance with one aspect of the present invention, there is provided a novel mature polypeptide, as well as biologically active and diagnostically or therapeutically useful fragments, analogs and derivatives thereof.

In accordance with another aspect of the present invention, there are provided isolated nucleic acid molecules encoding the polypeptide of the present invention including mRNAs, DNAs, cDNAs, genomic DNAs as well as analogs and biologically active and diagnostically or therapeutically useful fragments and derivatives thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process of utilizing such polypeptide, or polynucleotide encoding such polypeptide for therapeutic purposes, for example, to treat muscle wasting diseases, osteoporosis, to aid in implant fixation, to stimulate wound healing and tissue regeneration, to promote angiogenesis and to stimulate proliferation of vascular smooth muscle and endothelial cell production.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, to limit the production of excess connective tissue during wound healing or pulmonary fibrosis.

In accordance with yet a further aspect of the present invention, there are also provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to expression of the polypeptide of the present invention and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the cDNA (SEQ ID NO: 1) and corresponding deduced amino acid sequence (SEQ ID NO: 2) of the polypeptide of the present invention. The standard one letter abbreviations for amino acids are used. Sequencing was performed using a 373 Automated DNA sequencer (Applied Biosystems, Inc.).

FIG. 2 shows the amino acid sequence homology between the polypeptide of the present invention (top line) (SEQ ID NO: 2) and the cripto growth factor (bottom line) (SEQ ID NO: 7).

In accordance with an aspect of the present invention, there are provided isolated nucleic acids (polynucleotides) which encode for the mature polypeptide having the deduced amino acid sequence of FIG. 1 (SEQ ID NO: 2) or for the mature polypeptide encoded by the cDNA of the clone(s) deposited as ATCC Deposit No. 97142 on May 11, 1995.

The ATCC number referred to above is directed to a biological deposit with the ATCC, 10801 University Boulevard, Va. 20110-2209. The strain is being maintained under the terms of the Budapest Treaty and will be made available to a patent office signatory to the Budapest Treaty.

A polynucleotide encoding a polypeptide of the present invention was discovered in a cDNA library derived from human pancreatic cancer tissue. It is structurally related to the human cripto growth factor. It contains an open reading frame encoding a protein of 230 amino acid residues of which approximately the first 23 amino acids residues are the putative leader sequence such that the mature protein comprises 207 amino acids. As shown in FIG. 2 the polypeptide of the present invention has conserved cysteine residues in common with cripto growth factor.

Moreover, the polypeptide of the present invention has a putative soluble portion comprising amino acid 45 to amino acid 128 of SEQ ID NO: 2, such that amino acid 129 to amino acid 207 is a putative transmembrane portion.

An initial Northern blot analysis has shown very high expression in pancreatic cancer cells.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO: 1) or that of the deposited clone or may be a different coding sequence which coding sequence, as a result of the redundancy or degeneracy of the genetic code, encodes the same mature polypeptide as the DNA of FIG. 1 (SEQ ID NO: 1) or the deposited cDNA.

The polynucleotide which encodes for the mature polypeptide of FIG. 1 (SEQ ID No. 2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID No. 2) or the same mature polypeptide encoded by the cDNA of the deposited clone as well as variants of such polynucleotides which variants encode for a fragment, derivative or analog of the polypeptide of FIG. 1 (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO: 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37: 767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length CGF gene may be used as a hybridization probe for a cDNA library to isolate the full length CGF gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete CGF gene including regulatory and promotor regions, exons, and introns. An example of a screen comprises isolating the coding region of the CGF gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO: 1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO: 2 as well as fragments thereof, which fragments have at least 30 bases and preferably at least 50 bases and to polypeptides encoded by such polynucleotides.

The deposit(s) referred to herein were deposited with the ATCC (American Type Culture Collection, 10801 University Boulevard, Manassas, Va. 20110-2209) on May 11, 1995, and will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence or (v) splice variants of the mature polypeptide which are lacking certain amino acid residues yet still retain biological activity. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO: 2 (in particular the mature polypeptide) as well as polypeptides which have at least 70% similarity (preferably at least a 70% identity) to the polypeptide of SEQ ID NO: 2 and more preferably at least a 90% similarity (more preferably at least 90% identity) to the polypeptide of SEQ ID NO: 2 and still more preferably at least a 95% similarity (still more preferably at least a 95% identity) to the polypeptide of SEQ ID NO: 2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the CGF genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda P$_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pBSKS, pNH8A, pNH16a, pNH18A, pNH46A(Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda P$_R$, P$_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23: 175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The CGF gene of the present invention may be labeled and used as a probe for the analysis of Southern blots containing endonuclease digested DNA preparations to ascertain if there are amplification, rearrangement, deletions or restrictiion fragment length polymorphisms of the criptin gene in normal versus tumor tissue.

The labeled criptin gene can be employed for the analysis of Northern blots that contain RNA to determine the relative levels of mRNA expression in various normal and pathologic tissue sample.

The CGF gene may be employed to generate a probe suitable for in situ RNA:RNA hybridization for histologic localization in normal or pathologic cells expressing CGF mRNA.

CGF oligonucleotides (sense-strand) may be employed to detect levels of CGF mRNA in various tissues.

CGF polypeptide is over expressed and secreted by certain types of cancer cell, for example, pancreatic cancers. Therefore, detection of CGF gene transcription or an excessive amount of CGF protein allows a pancreatic cancer diagnosis. Accordingly, an anti-CGF antibody could be used to diagnose neovascularization associated with tumor formation since an altered level of this polypeptide may be indicative of such disorders.

A competition assay may be employed wherein antibodies specific to CGF are attached to a solid support and labeled CGF and a sample derived from the host are passed over the solid support and the amount of label detected attached to the solid support can be correlated to a quantity of CGF in the sample.

A "sandwich" assay is similar to an ELISA assay. In a "sandwich" assay the CGF polypeptide is passed over a solid support and binds to antibody attached to a solid support. A second antibody is then bound to the CGF polypeptide. A third antibody which is labeled and specific to the second antibody is then passed over the solid support and binds to the second antibody and an amount can then be quantified.

The polypeptide of the present invention may be employed in wound-healing and associated therapies concerned with re-growth of tissue, such as connective tissue, skin, bone, cartilage, muscle, lung or kidney.

The polypeptide may also be employed to stimulate angiogenesis, for example, to enhance the growth of vascular smooth muscle and endothelial cells. The increase in angiogenesis would be beneficial to ischemic tissues and to collateral coronary development in the heart subsequent to coronary stenosis.

The polypeptide of the present invention may also be employed during implant fixation to stimulate the growth of cells around the implant and therefore, facilitate its attachment to its intended site.

In accordance with yet a further aspect of the present invention, there is provided a process for utilizing such polypeptides, or polynucleotides encoding such polypeptides, as a research reagent for in vitro purposes related to scientific research, synthesis of DNA and manufacture of DNA vectors, for the purpose of developing therapeutics and diagnostics for the treatment of human disease.

This invention provides a method for identification of the receptor for the polypeptide of the present invention. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to CGF polypeptides, and a cDNA library created from this RNA is divided into pools and used to transfect COS cells or other cells that are not responsive to CGF. Transfected cells which are grown on glass slides are exposed to labeled CGF. CGF can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled CGF can be photoaffinity linked with cell membrane or extract preparations that express the receptor molecule. Cross-linked material is resolved by PAGE and exposed to X-ray film. The labeled complex containing the CGF-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention is also related to a method of screening compounds to identify those which bind to and activate the CGF receptors. An example of such a screening method measures stimulation of the proliferation of endothelial cells in the presence of the comitogen Con A. Human umbilical vein endothelial cells are obtained and cultured in 96-well flat-bottomed culture plates (Costar, Cambridge, Mass.) and supplemented with a reaction mixture appropriate for facilitating proliferation of the cells, the mixture containing Con-A (Calbiochem, La Jolla, Calif.). Con-A and the compound to be screened are added and after incubation at 37° C., cultures are pulsed with $^3$[H]thymidine and harvested onto glass fiber filters (PhD; Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]-thymidine incorporation indicates stimulation of endothelial cell proliferation.

To assay for antagonist compounds, the assay described above is performed, however, in this assay CGF is added along with the compound to be screened and the ability of the compound to inhibit $^3$[H]-thymidine incorporation in the presence of CGF, indicates that the compound is an antagonist to CGF.

Alternatively, CGF antagonists may be detected by combining labeled CGF and a potential antagonist compound with membrane-bound CGF receptors or recombinant receptors under appropriate conditions for a competitive inhibition assay. CGF can be labeled, such as by radioactivity, such that the number of CGF molecules bound to the receptor can determine the effectiveness of the potential antagonist.

Alternatively, the response of a known second messenger system following interaction of a potential antagonist compound and receptor would be measured. Such second messenger systems include but are not limited to, cAMP guanylate cyclase, ion channels or phosphoinositide hydrolysis. The compound may be labeled to detect binding. A compound which binds but which does not elicit a second messenger response is an effective antagonist compound.

Examples of potential CGF antagonist compounds include an antibody, or in some cases, an oligonucleotide, which binds to the polypeptide itself or to the receptor for the polypeptide. Alternatively, a potential antagonist may be a closely related protein, for example, a mutated form of CGF, which recognizes the CGF receptor but imparts no effect, thereby competitively inhibiting the action of CGF.

Another potential CGF antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6: 3073 (1979); Cooney et al, Science, 241: 456 (1988); and Dervan et al., Science, 251: 1360 (1991)), thereby preventing transcription and the production of CGF. The antisense RNA oligonucleotide hybridizes to the mRNA in vivo and blocks translation of the mRNA molecule into the CGF (antisense—Okano, J. Neurochem., 56: 560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of CGF.

Potential CGF antagonists include small molecules which bind to the active site of the polypeptide, the receptor binding site, or other growth factor binding site of the polypeptide thereby blocking the normal biological activity of CGF. Examples of small molecules include but are not limited to small peptides or peptide-like molecules.

The antagonists may be employed to inhibit tumor growth, directly or indirectly, e.g., by antagonizing CGF activity and/or antagonizing neovascularization and the neointimal proliferation of smooth muscle cells prevalent in atherosclerosis and restenosis subsequent to balloon angioplasty.

The antagonists may be employed in a composition with a pharmaceutically acceptable carrier, e.g., as hereinafter described.

The CGF polypeptides and antagonist compounds of the present invention may be employed in combination with a suitable pharmaceutical carrier. Such compositions comprise a therapeutically effective amount of the polypeptide or antagonist compound and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

CGF in combination with other growth factors including but not limited to, PDGF, IGF, FGF, EGF or TGF-β may accelerate physiological responses as seen in wound healing.

The CGF polypeptide and agonists and antagonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256: 495–497), the trioma technique, the human B-cell hybridoma technique (Kozbor et al., 1983, Immunology Today 4: 72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52: 456–457 (1973).

EXAMPLE 1

Bacterial Expression and Purification of CGF

The DNA sequence encoding CGF, ATCC # 97142, was initially amplified using PCR oligonucleotide primers corresponding to the 5' sequences of the processed CGF protein (minus the signal peptide sequence) and the vector sequences 3' to the CGF gene. Additional nucleotides corresponding to CGF were added to the 5' and 3' sequences respectively. The 5' oligonucleotide primer has the sequence 5' ACTCTTGGATCCAATTTGGGAAACAGC-TATCAAAGA 3' (SEQ ID NO: 3) contains a BamHI restriction enzyme site (in bold) followed by CGF coding sequence starting from the presumed terminal amino acid of the processed protein codon (underlined). The 3' oligonucleotide primer 5' TACAA CTCTAGACTATTATTTACAA-CATAGAAAATTAAAGGC 3' (SEQ ID NO: 4) contains an Xba I restriction site (in bold) followed by the reverse complement of nucleotides corresponding to the carboxy-terminal 5 amino acids and the translational stop codon (underlined). The restriction enzyme sites correspond to the restriction enzyme sites on the bacterial expression vector pQE (Qiagen, Inc. Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with Hind III and Xba I. The amplified sequences were ligated into pQE-9 and were inserted in frame with the sequence encoding for the histidine tag and the RBS. The desired recombinants would contain the CGF coding sequence inserted downstream from the histidine tag and the ribosome binding site. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 2.5 hours such that there is an exponential growth culture present. Cells were then harvested by centrifugation. The CGF/6-Histidine-containing M15[pREP4] cells were lysed in 6M GnHCl,50 mM NaPO$_4$ at pH 8.0. The lysate was loaded on a Nickel-Chelate column and the flow-through collected. The column was washed with 6M GnHCl, 50 mM NaPO$_4$ at pH 8.0, 6.0 and 5.0. The CGF fusion protein (>90% pure) was eluted at pH 2.0. For the purpose of renaturation, the pH 2.0 eluate was adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate. To run the gel, the pellets were resuspended in SDS/NaOH and 2X SDS-PAGE loading buffer, heat denatured, then electrophoresed on a 4–20% SDS-PAGE gel. The proteins were visualized with Coomassie Brilliant Blue R-250 stain.

EXAMPLE 2

Cloning and expression of CGF using the baculovirus expression system

The DNA sequence encoding the full length CGF protein, ATCC # 97142, is amplified with the PCR primers containing 5' BamHI and 3' XbaI. The primer sequences are 5' ACTCTTGGATCC GCCATCATGACCTGGAGGCACCAT 3' (SEQ ID NO: 5) and 5' TACAA CTCTAGACTATTATTTACAACATAGAAAATTAAAGGC 3' (SEQ ID NO: 4). The BamHI-XbaI fragment contains the entire CGF coding region including the signal sequence for secretion. This fragment, designated F2, is isolated from a 1% agarose gel using a commercially available kit ("Geneclean", BIO 101 Inc., La Jolla, Calif.).

The vector pA2 is used for the expression of the CGF protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhidrosis virus (AcMNPV) followed by the recognition sites for the restriction endonucleases BamHI and XbaI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pA2 such as, pRG1, pAc373, pVL941 and pAcIM1 (Luckow, V. A. and Summers, M. D., Virology, 170: 31–39).

The pA2 plasmid is digested with the restriction enzymes BamHI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

BamHI-XbaI cleaved fragment F2 and the dephosphorylated plasmid V2 are ligated with T4 DNA ligase. *E. coli* strain XL1 Blue (Stratagene Cloning Systems, 11011 North Torrey Pines Road La Jolla, Calif. 92037) are then transformed and bacteria identified that contained the plasmid (pBac CGF) with the CGF cDNA using the enzymes BamHI and XbaI. The sequence of the cloned fragment is confirmed by DNA sequencing.

5 $\mu$g of the plasmid pBac CGF is cotransfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. USA, 84: 7413–7417 (1987)).

1 $\mu$g of BaculoGold™ virus DNA and 5 $\mu$g of the plasmid pBac CGF are mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 $\mu$l of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-CGF at a multiplicity of infection (MOI) of 2. Six hours later the medium is removed and replaced with SF900 II medium minus methionine and cysteine (Life Technologies Inc., Gaithersburg). 42 hours later 5 $\mu$Ci of $^{35}$S-methionine and 5 $\mu$Ci $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant CGF in CHO cells

The vector pN346 is used for the expression of the CGF protein. Plasmid pN346 is a derivative of the plasmid pSV2-dhfr [ATCC Accession No. 37146]. Both plasmids contain the mouse dhfr gene under control of the SV40 early promoter. Chinese hamster ovary or other cells lacking dihydrofolate activity that are transfected with these plasmids can be selected by growing the cells in a selective medium (alpha minus MEM, Lift Technologies) supplemented with the chemotherapeutic agent methotrexate. The amplication of the DHFR genes in cells resistant to methotrexate (MTX) has been well documented (see, e.g., Alt, F.

W., Kellems, R. M., Bertino, J. R., and Schimke, R. T., 1978, J. Biol. Chem. 253: 1357–1370, Hamlin, J. L. and Ma, C. 1990, Biochem. et Biophys. Acta, 1097: 107–143, Page, M. J. and Sydenham, M. A. 1991, Biotechnology Vol. 9: 64–68). Cells grown in increasing concentrations of MTX develop resistance to the drug by overproducing the target enzyme, DHFR, as a result of amplification of the DHFR gene. If a second gene is linked to the dhfr gene it is usually co-amplified and overexpressed. Subsequently, when the methotrexate is withdrawn, cell lines contain the amplified gene integrated into the chromosome(s).

Plasmid pN346 contains for the expression of the gene of interest a strong promoter of the long terminal repeat (LTR) of the Rouse Sarcoma Virus (Cullen, et al., Molecular and Cellular Biology, March 1985, 438–447) plus a fragment isolated from the enhancer of the immediate early gene of human cytomegalovirus (CMV) (Boshart et al., Cell 41: 521–530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g. G418 plus methotrexate.

The plasmid pN346 is digested with the restriction enzyme BamHI and then dephosphorylated using calf intestinal phosphatase by procedures known in the art. The vector is then isolated from a 1% agarose gel.

The DNA sequence encoding the full length CGF protein, ATCC # 97142, is amplified using PCR oligonucleotide primers corresponding to the 5' and 3' sequences of the gene:

The 5' primer has the sequence 5' ACTCTTGGATCC GCCATCATGACCTGGAGGCACCAT 3' (SEQ ID NO: 5) and contains a BamHI restriction enzyme site (in bold) followed by 6 nucleotides resembling an efficient signal for the initiation of translation in eukaryotic cells (Kozak, M., J. Mol. Biol., 196: 947–950, (1987)). The remaining nucleotides correspond to the amino terminal 6 amino acids including the translational initiation codon. The 3' primer has the sequence 5' TACAACCAGCTGCTATTATTTA-CAACATAG 3' (SEQ ID NO: 6) and contains a PvuII restriction site and 18 nucleotides that are the reverse complement of 3' CGF DNA starting at the translational stop codon. The PCR product is digested with BamHI-PvuII and purified on a 1% agarose gel using a commercially available kit ("Geneclean", BIO 101 Inc., La Jolla, Calif.). This fragment is then ligated to BamHI-PvuII digested, phosphatased pN346 plasmid with T4 DNA ligase. Xl1 Blue (Stratagene) $E.$ $coli$ are transformed and plated on LB, 50 μg/ml ampicillin plates. Colonies bearing the desired recombinant in the proper orientation are screened for by PCR with a 5' primer which corresponds to the Rous sarcoma virus promoter and a 3' primer which corresponds to the reverse complement of CGF codons 73–79. The sequence of the cloned fragment is confirmed by DNA sequencing. Transfection of CHO-dhfr-cells Chinese hamster ovary cells lacking an active DHFR enzyme are used for transfection. 5 μg of the expression plasmid pN346CGF are cotransfected with 0.5 μg of the plasmid pSVneo using the lipofectin method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25, 50 nm, 100 nm, 200 nm, 400 nm). Clones growing at the highest concentrations of methotrexate are then transferred to new 6-well plates containing even higher concentrations of methotrexate (500 nM, 1 μM, 2 μM, 5 μM). The same procedure is repeated until clones grew at a concentration of 100 μM.

The expression of the desired gene product is analyzed by Western blot analysis and SDS-PAGE.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7: 219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer also includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated nucleic acid molecule comprising a polynucleotide selected from the group consisting of:
   (a) a polynucleotide encoding amino acids 1 to 230 of SEQ ID NO: 2;
   (b) a polynucleotide encoding the complete amino acid sequence encoded by the cDNA clone contained in ATCC Deposit No. 97142;
   (c) a polynucleotide encoding amino acids 24 to 230 of SEQ ID NO: 2;
   (d) a polynucleotide encoding the mature form of the polypeptide encoded by the cDNA clone contained in ATCC Deposit No. 97142;
   (e) a polynucleotide encoding amino acids 129 to 207 of SEQ ID NO: 2;
   (f) a polynucleotide encoding amino acids 45 to 128 of SEQ ID NO: 2;
   (g) a polynucleotide encoding amino acids 1 to 173 of SEQ ID NO: 2;
   (h) a polynucleotide encoding amino acids 24 to 173 of SEQ ID NO: 2;
   (i) a polynucleotide encoding amino acids 68 to 173 of SEQ ID NO: 2;
   (j) a polynucleotide encoding amino acids 24 to 67 of SEQ ID NO:2;
   (k) a polynucleotide encoding amino acids 174 to 230 of SEQ ID NO: 2; and
   (l) a polynucleotide which is complementary to the polynucleotide of (a), (b), (c), (d), (e), (f), (g), (h), (i), (j), or (k).

2. The isolated nucleic acid molecule of claim 1 wherein said nucleic acid comprises a polynucleotide encoding amino acids 1 to 230 of SEQ ID NO: 2.

3. The isolated nucleic acid molecule of claim 1 wherein said nucleic acid comprises a polynucleotide encoding the complete amino acid sequence encoded by the cDNA clone contained in ATCC Deposit No. 97142.

4. The isolated nucleic acid molecule of claim 1 wherein said nucleic acid comprises a polynucleotide encoding amino acids 24 to 230 of SEQ ID NO: 2.

5. The isolated nucleic acid molecule of claim 1 wherein said nucleic acid comprises a polynucleotide encoding the mature form of the polypeptide encoded by the cDNA clone contained in ATCC Deposit No. 97142.

6. The isolated nucleic acid molecule of claim 1 wherein said nucleic acid comprises a polynucleotide encoding amino acids 129 to 207 of SEQ ID NO: 2.

7. The isolated nucleic acid molecule of claim 1 wherein said nucleic acid comprises a polynucleotide encoding amino acids 45 to 128 of SEQ ID NO: 2.

8. The isolated nucleic acid molecule of claim 1 wherein said nucleic acid comprises a polynucleotide encoding amino acids 1 to 173 of SEQ ID NO: 2.

9. The isolated nucleic acid molecule of claim 1 wherein said nucleic acid comprises a polynucleotide encoding amino acids 24 to 173 of SEQ ID NO: 2.

10. The isolated nucleic acid molecule of claim 1 wherein said nucleic acid comprises a polynucleotide encoding amino acids 68 to 173 of SEQ ID NO: 2.

11. The isolated nucleic acid molecule of claim 1 wherein said nucleic acid comprises a polynucleotide encoding amino acids 24 to 67 of SEQ ID NO: 2.

12. The isolated nucleic acid molecule of claim 1 wherein said nucleic acid comprises a polynucleotide encoding amino acids 174 to 230 of SEQ ID NO: 2.

13. The isolated nucleic acid molecule of claim 1 wherein said nucleic acid comprises a polynucleotide which is complementary to the polynucleotide of (a), (b), (c), (d), (e), (f), (g), (h), (i), (j), or (k).

14. A recombinant vector comprising the nucleic acid of claim 1.

15. A recombinant vector comprising the nucleic acid of claim 1 operably associated with a heterologous regulatory sequence that controls gene expression.

16. A genetically engineered host cell comprising the nucleic acid of claim 1.

17. A genetically engineered host cell comprising the nucleic acid of claim 1 operatively associated with a heterologous regulatory sequence that controls gene expression.

18. A recombinant method for producing a polypeptide, comprising culturing the genetically engineered host cell of claim 17 under conditions such that said polypeptide is expressed and recovering said polypeptide.

19. The isolated nucleic acid molecule of claim 1 fused to a heterologous polynucleotide.

20. The isolated nucleic acid molecule of claim 19 wherein said heterologous polynucleotide encodes a heterologous polypeptide.

21. An isolated nucleic acid molecule comprising at polynucleotide encoding at least 30 contiguous amino acids of SEQ ID NO: 2.

22. The isolated nucleic acid molecule of claim 21, wherein said polynucleotide encodes at least 50 contiguous amino acids of SEQ ID NO: 2.

23. A recombinant vector comprising the nucleic acid of claim 21.

24. A recombinant vector comprising the nucleic acid of claim 21 operably associated with a heterologous regulatory sequence that controls gene expression.

25. A genetically engineered host cell comprising the nucleic acid of claim 21.

26. A genetically engineered host cell comprising the nucleic acid of claim 21 operatively associated with a heterologous regulatory sequence that controls gene expression.

27. A recombinant method for producing a polypeptide, comprising culturing the genetically engineered host cell of claim 26 under conditions such that said polypeptide is expressed and recovering said polypeptide.

28. The isolated nucleic acid molecule of claim 21 fused to a heterologous polynucleotide.

29. The isolated nucleic acid molecule of claim 28 wherein said heterologous polynucleotide encodes a heterologous polypeptide.

30. An isolated polypeptide comprising an amino acid sequence selected from the group consisting of:
    (a) amino acids 1 to 230 of SEQ ID NO: 2;
    (b) the complete amino acid sequence encoded by the cDNA clone contained in ATCC Deposit No. 97142;
    (c) amino acids 24 to 230 of SEQ ID NO: 2;
    (d) the mature form of the polypeptide encoded by the cDNA clone contained in ATCC Deposit No. 97142;
    (e) amino acids 129 to 207 of SEQ ID NO: 2;
    (f) amino acids 45 to 128 of SEQ ID NO: 2;
    (g) amino acids 1 to 173 of SEQ ID NO: 2;
    (h) amino acids 24 to 173 of SEQ ID NO: 2;
    (i) amino acids 68 to 173 of SEQ ID NO: 2;
    (j) amino acids 24 to 67 of SEQ ID NO: 2; and
    (k) amino acids 174 to 230 of SEQ ID NO: 2.

31. The isolated polypeptide of claim 30 wherein said polypeptide comprises amino acids 1 to 230 of SEQ ID NO: 2.

32. The isolated polypeptide of claim 30 wherein said polypeptide comprises the complete amino acid sequence encoded by the cDNA clone contained in ATCC Deposit No. 97142.

33. The isolated polypeptide of claim 30 wherein said polypeptide comprises amino acids 24 to 230 of SEQ ID NO: 2.

34. The isolated polypeptide of claim 30 wherein said polypeptide comprises the mature form of the polypeptide encoded by the cDNA clone contained in ATCC Deposit No. 97142.

35. The isolated polypeptide of claim 30 wherein said polypeptide comprises amino acids 129 to 207 of SEQ ID NO: 2.

36. The isolated polypeptide of claim 30 wherein said polypeptide comprises amino acids 45 to 128 of SEQ ID NO: 2.

37. The isolated polypeptide of claim 30 wherein said polypeptide comprises amino acids 1 to 173 of SEQ ID NO: 2.

38. The isolated polypeptide of claim 30 wherein said polypeptide comprises amino acids 24 to 173 of SEQ ID NO: 2.

39. The isolated polypeptide of claim 30 wherein said polypeptide comprises amino acids 68 to 173 of SEQ ID NO: 2.

40. The isolated polypeptide of claim 30 wherein said polypeptide comprises amino acids 24 to 67 of SEQ ID NO: 2.

41. The isolated polypeptide of claim 30 wherein said polypeptide comprises amino acids 174 to 230 of SEQ ID NO: 2.

42. A fusion protein comprising the isolated polypeptide of claim 30 fused to a heterologous polypeptide.

43. A composition comprising the polypeptide of claim 30 and a pharmaceutically acceptable carrier.

44. An isolated polypeptide comprising at least 10 contiguous amino acids of SEQ ID NO: 2.

45. The isolated polypeptide of claim 44 wherein said polypeptide comprises at least 30 contiguous amino acids of SEQ ID NO: 2.

46. The isolated polypeptide of claim 44 wherein said polypeptide comprises at least 50 contiguous amino acids of SEQ ID NO: 2.

47. A fusion protein comprising the isolated polypeptide of claim 44 fused to a heterologous polypeptide.

48. A composition comprising the polypeptide of claim 44 and a pharmaceutically acceptable carrier.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 774 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 82..771

(xi) SEQUENCE DESCRIPTION: SEQ ID NO:1:

```
ATGCAGAAGA CTCTTCAAGA TTCAGCTTTC CTGGAAACTG ATCTTCAATG CACTAAGAGA        60

AGGAGACTCT CAAACCCAAA A ATG ACC TGG AGG CAC CAT GTC AGG CTT CTG        111
                        Met Thr Trp Arg His His Val Arg Leu Leu
                         1               5                  10

TTT ACG GTC AGT TTG GCA TTA CAG ATC ATC AAT TTG GGA AAC AGC TAT        159
Phe Thr Val Ser Leu Ala Leu Gln Ile Ile Asn Leu Gly Asn Ser Tyr
             15                  20                  25

CAA AGA GAG AAA CAT AAC GGC GGT AGA GAG GAA GTC ACC AAG GTT GCC        207
Gln Arg Glu Lys His Asn Gly Gly Arg Glu Glu Val Thr Lys Val Ala
         30                  35                  40

ACT CAG AAG CAC CGA CAG TCA CCG CTC AAC TGG ACC TCC AGT CAT TTC        255
Thr Gln Lys His Arg Gln Ser Pro Leu Asn Trp Thr Ser Ser His Phe
     45                  50                  55

GGA GAG GTG ACT GGG AGC GCC GAG GGC TGG GGG CCG GAG GAG CCG CTC        303
Gly Glu Val Thr Gly Ser Ala Glu Gly Trp Gly Pro Glu Glu Pro Leu
 60                  65                  70

CCC TAC TCC CGG GCT TTC GGA GAG GGT GCG TCC GCG CGG CCG CGC TGC        351
Pro Tyr Ser Arg Ala Phe Gly Glu Gly Ala Ser Ala Arg Pro Arg Cys
 75                  80                  85                  90

TGC AGG AAC GGC GGT ACC TGC GTG CTG GGC AGC TTC TGC GTG TGC CCG        399
Cys Arg Asn Gly Gly Thr Cys Val Leu Gly Ser Phe Cys Val Cys Pro
                 95                 100                 105

GCC CAC TTC ACC GGC CGC TAC TGC GAG CAT GAC CAG AGG CGC AGT GAA        447
Ala His Phe Thr Gly Arg Tyr Cys Glu His Asp Gln Arg Arg Ser Glu
            110                 115                 120

TGC GGC GCC CTG GAG CAC GGA GCC TGG ACC CTC CGC GCC TGC CAC CTC        495
Cys Gly Ala Leu Glu His Gly Ala Trp Thr Leu Arg Ala Cys His Leu
        125                 130                 135

TGC AGG TGC ATC TTC GGG GCC CTG CAC TGC CTC CCC CTC CAG ACG CCT        543
Cys Arg Cys Ile Phe Gly Ala Leu His Cys Leu Pro Leu Gln Thr Pro
    140                 145                 150

GAC CGC TGT GAC CCG AAA GAC TTC CTG GCC TCC CAC GCT CAC GGG CCG        591
```

```
Asp Arg Cys Asp Pro Lys Asp Phe Leu Ala Ser His Ala His Gly Pro
155                 160                 165                 170

AGC GCC GGG GGC GCG CCC AGC CTG CTA CTC TTG CTG CCC TGC GCA ACT      639
Ser Ala Gly Gly Ala Pro Ser Leu Leu Leu Leu Leu Pro Cys Ala Thr
                175                 180                 185

CCT GCA CCG GCC TCC TGC GCC CGG ATG CGC CCG CGC ACC CTC GGT CCC      687
Pro Ala Pro Ala Ser Cys Ala Arg Met Arg Pro Arg Thr Leu Gly Pro
            190                 195                 200

TGG TCC CTT CCG TCC TCC AGC GGG AGC GGC GCC CCT GCG GAA GGC CGG      735
Trp Ser Leu Pro Ser Ser Ser Gly Ser Gly Ala Pro Ala Glu Gly Arg
        205                 210                 215

GAC TTG GGC ATC GCC TTT AAT TTT CTA TGT TGT AAA TAA                  774
Asp Leu Gly Ile Ala Phe Asn Phe Leu Cys Cys Lys
    220                 225                 230
```

(2) INFORMATION FOR SEQ ID NO:2:

(i) SEQUENCE CHARACTERISTICS:
        (A) LENGTH: 230 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Trp Arg His His Val Arg Leu Leu Phe Thr Val Ser Leu Ala
1               5                   10                  15

Leu Gln Ile Ile Asn Leu Gly Asn Ser Tyr Gln Arg Glu Lys His Asn
            20                  25                  30

Gly Gly Arg Glu Glu Val Thr Lys Val Ala Thr Gln Lys His Arg Gln
        35                  40                  45

Ser Pro Leu Asn Trp Thr Ser Ser His Phe Gly Glu Val Thr Gly Ser
    50                  55                  60

Ala Glu Gly Trp Gly Pro Glu Pro Leu Pro Tyr Ser Arg Ala Phe
65                  70                  75                  80

Gly Glu Gly Ala Ser Ala Arg Pro Arg Cys Cys Arg Asn Gly Gly Thr
                85                  90                  95

Cys Val Leu Gly Ser Phe Cys Val Cys Pro Ala His Phe Thr Gly Arg
            100                 105                 110

Tyr Cys Glu His Asp Gln Arg Arg Ser Glu Cys Gly Ala Leu Glu His
        115                 120                 125

Gly Ala Trp Thr Leu Arg Ala Cys His Leu Cys Arg Cys Ile Phe Gly
    130                 135                 140

Ala Leu His Cys Leu Pro Leu Gln Thr Pro Asp Arg Cys Asp Pro Lys
145                 150                 155                 160

Asp Phe Leu Ala Ser His Ala His Gly Pro Ser Ala Gly Gly Ala Pro
                165                 170                 175

Ser Leu Leu Leu Leu Pro Cys Ala Thr Pro Ala Pro Ala Ser Cys
            180                 185                 190

Ala Arg Met Arg Pro Arg Thr Leu Gly Pro Trp Ser Leu Pro Ser Ser
        195                 200                 205

Ser Gly Ser Gly Ala Pro Ala Glu Gly Arg Asp Leu Gly Ile Ala Phe
    210                 215                 220

Asn Phe Leu Cys Cys Lys
225                 230
```

(2) INFORMATION FOR SEQ ID NO:3:

(i) SEQUENCE CHARACTERISTICS:

(A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:3:

ACTCTTGGAT CCAATTTGGG AAACAGCTAT CAAAGA                                36

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:4:

TACAACTCTA GACTATTATT TACAACATAG AAAATTAAAG GC                         42

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:5:

ACTCTTGGAT CCGCCATCAT GACCTGGAGG CACCAT                                36

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:6:

TACAACCAGC TGCTATTATT TACAACATAG                                       30

(2) INFORMATION FOR SEQ ID NO:7:

(i) SEQUENCE CHARACTERISTICS:
        (A) LENGTH: 188 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Met Asp Cys Arg Lys Met Ala Arg Phe Ser Tyr Val Ile Trp Ile
 1               5                  10                  15

Met Ala Ile Ser Lys Val Phe Glu Leu Gly Leu Val Ala Gly Leu Gly
             20                  25                  30

His Gln Glu Phe Ala Arg Pro Ser Arg Gly Tyr Leu Ala Phe Arg Asp

-continued

```
                35                      40                      45

Asp Ser Ile Trp Pro Gln Glu Glu Pro Ala Ile Arg Pro Arg Ser Ser
         50                      55                      60

Gln Arg Val Pro Pro Met Gly Ile Gln His Ser Lys Glu Leu Asn Arg
 65                      70                      75                  80

Thr Cys Cys Leu Asn Gly Gly Thr Cys Met Leu Gly Ser Phe Cys Ala
                 85                      90                      95

Cys Pro Pro Ser Phe Tyr Gly Arg Asn Cys Glu His Asp Val Arg Lys
                100                     105                    110

Glu Asn Cys Gly Ser Val Pro His Asp Thr Trp Leu Pro Lys Lys Cys
            115                     120                    125

Ser Leu Cys Lys Cys Trp His Gly Gln Leu Arg Cys Phe Pro Gln Ala
        130                     135                    140

Phe Leu Pro Gly Cys Asp Gly Leu Val Met Asp Glu His Leu Val Ala
145                     150                    155                 160

Ser Arg Thr Pro Glu Leu Pro Pro Ser Ala Arg Thr Thr Thr Phe Met
                165                     170                    175

Leu Val Gly Ile Cys Leu Ser Ile Gln Ser Tyr Tyr
                180                     185
```